United States Patent
Denner et al.

(10) Patent No.: US 9,310,259 B2
(45) Date of Patent: Apr. 12, 2016

(54) METHOD FOR PERFORMING A DIFFERENTIAL THERMAL ANALYSIS

(71) Applicant: Netzsch-Gerätebau GmbH, Selb (DE)

(72) Inventors: Thomas Denner, Selb (DE); Juergen Blumm, Selb (DE); Otto Max Schaefer, Selb (DE); Markus Hollering, Wunsiedel (DE); Thilo Hilpert, Selb (DE); Alexander Frenzl, Schoenwald (DE); Stefan Lauterbach, Selb (DE); Andreas Strobel, Auerbach (DE); Rolf Preuss, Einbeck (DE); Michael Gebhardt, Selb (DE); Elena Moukhina, Selb (DE); Alexander Schindler, Leupoldsgruen (DE); Mathias Gradl, Sesslach (DE); Gunter Herr, Haarth (DE); Stephan Knappe, Doehlau (DE); Markus Meyer, Ehingen (DE); Gabriele Kaiser, Selb (DE); Andre Nijmeh, Merkendorf (DE)

(73) Assignee: Netzsch-Gerätebau GmbH, Selb (DE)

( * ) Notice: Subject to any disclaimer, the term of this patent is extended or adjusted under 35 U.S.C. 154(b) by 145 days.

(21) Appl. No.: 14/163,714

(22) Filed: Jan. 24, 2014

(65) Prior Publication Data
US 2014/0204971 A1   Jul. 24, 2014

(51) Int. Cl.
| | |
|---|---|
| *G01N 25/00* | (2006.01) |
| *G01K 17/00* | (2006.01) |
| *G01K 3/14* | (2006.01) |
| *G01N 25/48* | (2006.01) |

(52) U.S. Cl.
CPC ............... *G01K 3/14* (2013.01); *G01N 25/4866* (2013.01)

(58) Field of Classification Search
CPC .... G01N 25/4866; G01N 25/00; G01K 17/00
USPC .......................................................... 374/10
See application file for complete search history.

(56) References Cited

FOREIGN PATENT DOCUMENTS

DE        19934448 A1 *  8/2000   ......... G01N 25/4833

\* cited by examiner

*Primary Examiner* — Lisa Caputo
*Assistant Examiner* — Jamel Williams
(74) *Attorney, Agent, or Firm* — Whitmyer IP Group LLC

(57) ABSTRACT

A method for conducting a differential thermal analysis, in which a sample disposed in a temperable sample space is tempered according to an essentially linear temperature program extending from a start temperature to an end temperature, such that, from the result of a measurement of the sample temperature conducted during tempering at a number of measurement time points, a DTA signal is calculated as the difference between a measured sample temperature and a reference temperature calculated according to a temperature curve model. According to the invention, for every measurement time point, the relevant reference temperature is calculated by the following steps: (a) establish a time interval containing the relevant measurement time point; (b) calculate a non-linear adjustment function for the measured sample temperature curve in the time interval; and (c) calculate the reference temperature as a value of the adjustment function for the measurement time point.

10 Claims, 2 Drawing Sheets

METHOD FOR PERFORMING A DIFFERENTIAL THERMAL ANALYSIS

FIELD OF THE INVENTION

The present invention relates to a method for performing a differential thermal analysis, often referred to as "DTA."

BACKGROUND OF THE INVENTION

In a generic method of this type, also more narrowly designated as "calculated differential thermal analysis" method or c-DTA method, a sample disposed in a temperable test space is tempered according to an essentially linear temperature program, extending from a start temperature to an end temperature. From the result of measuring the trial temperature at a number of measurement time points during tempering, a so-called c-DTA signal is calculated as the difference between measured trial temperature and a reference temperature calculated according to a temperature curve model.

A c-DTA method of this type is known from DE 199 34 448 A1. In this known method, a sample is heated or cooled according to a linear temperature program (that is, with an essentially stable temperature modification rate), extending from a start temperature $T_S$ to a final temperature $T_F$. During this tempering, the sample temperature is measured and stored by means of a sample thermal element.

From the start temperature $T_S$, the final temperature $T_F$ and the relevant time points, that is a start time $t_S$ and end time $t_F$, a median tempering rate (heating rate or cooling rate) $\beta$ can be calculated as follows:

$$\beta = (T_F - T_S)/(t_F - t_S) \qquad \text{(equation 1)}$$

According to the linear temperature program, a temperature curve model and/or a "calculated sample temperature" $T_C$ can be indicated in simple manner for each time point t as follows:

$$T_C(t) = T_S + \beta \times (t - t_S) \qquad \text{(equation 2)}$$

A DTA signal c-DTA(t) required as the result of the differential thermal analysis is then calculated as the difference between the sample temperature T(t) measured by means of the sample thermal element and the reference temperature $T_C(t)$ calculated according to equation 2:

$$c\text{-}DTA(t) = TC(t) - T(t)$$

A c-DTA signal not equal to zero indicates thermal effects in the sample, for example heat tones (changes in enthalpy) on account of phase transitions or the like. It is effects like these that are primarily of particular interest in the context of a differential thermal analysis and are recognizable in the course of the c-DTA signal.

It should be stated at this point that in differential thermal analyses of the type that is of interest here, other parameters or sample features (e.g., mass modifications of the sample, etc.) besides the sample temperature can also be measured in time-dissolved manner (and stored) during tempering, approximately at the same measuring time points as in the sample temperature measurements.

Although such additional measurements, which can be selected or concretely configured by referring to the general state of the art concerning differential thermal analyses, are also preferred in the context of the inventive method, this is still of rather secondary importance for the invention. The crux of the invention is the manner in which the c-DTA signal is ascertained on the basis of the time-dissolved sample temperature measured during tempering.

A disadvantage in the method known from DE 199 34 448 A1 is that a c-DTA signal not equal to zero can also result from a non-linearity of the temperature program, that is, a temperature that changes non-linearly over time. Thus, in the known method, a non-linear temperature program unavoidable in practice leads to a corresponding distortion of the c-DTA signal, which ideally is intended only to represent or reveal the thermal effects in the sample.

In order primarily to depict the thermal effects with the c-DTA signal, the main consideration, as likewise disclosed in DE 199 34 448 A1, is to assess the measured sample temperature or to calculate the c-DTA signal only for a (relatively small) segment of the entire duration of the temperature program. In this case, the influence of non-linearity of the (entire) temperature curve is rather limited. Disadvantageously then, however, the c-DTA signal is obtained only for this relatively small partial area.

SUMMARY OF THE INVENTION

It is therefore an object of the present invention in a differential thermal analysis method of the aforementioned type, to improve the quality of the obtained c-DTA signal in particular also in the presence of a non-ideal linear tempering and/or in determining the c-DTA signal over a great portion of the tempering duration or over the entire duration of the tempering.

This object is achieved according to the invention in that, for every measurement time point, the related reference temperature is calculated by the following steps:
a) establish a time interval that contains the relevant measurement time point,
b) calculate a non-linear adjustment function for the measured sample temperature curve in the time interval, and
c) calculate the reference temperature as a value of the adjustment function for the measurement time point.

The basic idea of the invention thus consists in calculating for every temperature measurement point its own adjustment curve (adjustment function) that serves as reference temperature, such that temperature data measured for this purpose are taken into account before the relevant temperature measurement point and/or after the temperature measurement point, namely in a predetermined time interval which contains the temperature measurement time point, and such that a non-linear adjustment function is used in the process.

A time interval containing the relevant measurement time point can advantageously be ascertained in automated manner (e.g., program-controlled in the context of a measuring program). This contributes advantageously to a reduction of the impact of the non-linearity, which is unavoidable in practice, on the calculation result. Any non-linearity still noticeable for the portion of the "relatively brief" time interval is then advantageously compensated or eliminated, at least in part, by the use of a non-linear adjustment function. Finally, by such individually conducted calculations for additional measurement time points, the c-DTA signal, which has been qualitatively improved according to the invention, can advantageously be obtained, without hesitation, for greater portions extending to the entire duration of the temperature program.

The tempering can involve either heating or cooling of the sample. The temperature program can foresee a difference between start and end temperatures of at least 50 K, for example.

The tempering rate averaged over the entire duration of the temperature program can be situated, for example, in the range of 1 to 50 K/min.

The measurement time points foreseen in the course of the temperature program can be set up equidistant from one another in time, for example with a measurement rate of at least 6 measurements/minute or at least 1 measurement/second.

More than 50 sample temperature measurements, for example, in particular more than 100, can be conducted and stored over the entire duration of the temperature program. This total number of measurement time points can be selected in practice, for example, depending on temperature range, heating rate and recording rate. A maximum total of 5,000 measurement time points, in particular a maximum of 2,000, is advantageously sufficient to limit the data quantity and for many application cases.

One embodiment foresees that in step a) the start of the time interval is set one time span before the relevant measurement time point, said time span being dependent on the measurement time point. For example, the later the relevant measurement time point is situated, the greater this time span can be. In particular, the time span can be established, for instance, proportionally to the measurement time point (time of the relevant measurement, based on the start time point of the temperature program). The proportionality factor here can be situated in particular in the range from 0.1 to 0.6, more preferably in the range from 0.2 to 0.5. This advantageously takes into account the circumstance that in practice the non-linearity of the tempering curve is somewhat great at the beginning and decreases somewhat in the time curve.

One embodiment foresees that in step a) the end of the time interval is set one time span after the relevant measurement time point, said time span being dependent on the measurement time point. For example, the later the relevant measurement time point is situated, the greater this time span can be. In particular, the time span can be established, for instance, proportionally to the measurement time point (based on the start time point of the temperature program). The proportionality factor here can be situated in particular in the range from 0.1 to 0.6, more preferably in the range from 0.2 to 0.5.

One embodiment foresees that in step a) the length of the time interval is set depending on the measurement time point. For example, the later the relevant measurement time point is situated, the greater this time span can be. In particular, the time span can be established, for instance, proportionally to the measurement time point (based on the start time point of the temperature program). The proportionality factor here can be situated in particular in the range from 0.4 to 0.9, more preferably in the range from 0.5 to 0.8.

One embodiment foresees that in step a), in the case of a time interval that extends before the start time point or after the end time point of the temperature program, an extrapolation, preferably a linear extrapolation, is performed for the execution of step b) of the sample temperatures that are to be used before the start time point or after the end time point. This makes it possible in simple manner, in particular, to calculate the c-DTA signal for the entire duration of the temperature program.

In a preferred embodiment, a second-degree polynomial is used as the adjustment function in step b). Although more complex adjustment functions ("fit functions") can be used in the context of the invention, in practice it has proved almost completely sufficient to use a second-degree polynomial, by means of which therefore the reference temperature curve, modeled by a simple straight line in the art, is replaced with a parabolic-shaped reference temperature curve.

According to a refinement of the invention, step b), herein also referred to as b1), is supplemented by the following steps:

b2) suppress measurement time points for which the measured sample temperature diverges from the relevant value of the adjustment function by more than a predetermined amount, and b3) calculate a corrected adjustment function for use in step c) as in step b1), but disregarding or underweighting the suppressed measurement points.

By means of these additional steps b2) and b3), an improvement or correction is achieved to some extent in the adjustment function previously calculated (in step b1). Preferably a second-degree polynomial is again used as adjustment function in the calculation according to step b3). However, in the adjustment or fit algorithm employed, the measurement time points or measurements selected or suppressed in step b2) are either completely disregarded, as though these measurements were totally nonexistent, or are given less weight by the relevant algorithm (e.g., normal weighting: 1; weighting of the suppressed measurement points: 0.5 or less).

One embodiment foresees that in step b1) the calculation of the adjustment function is performed while taking into account a weighting of the sample temperatures situated in the time interval.

A maximum value of the weighting function used for this purpose is here preferably given for the relevant measurement time point or in the proximity of this measurement time point, for example no farther removed from this measurement time point than by 20% of the time interval length.

The weighting (value of the weighting function) preferably decreases monotonically or strictly monotonically with increasing time distance from the relevant maximum time point.

In one embodiment, a Gaussian function is foreseen as the weighting function, for instance a Gaussian function (comprising a maximum) essentially centered on the relevant measurement time point (the maximum here can be situated, for example, precisely at the measurement time point or, for example, removed from it by less than 20% of the time interval length).

According to a refinement, the width of such a Gaussian function, or of other similar weighting function declining on both sides of the relevant measurement time point monotonically or strictly monotonically, is foreseen as dependent on the measurement time point (based on the start time point). For example, there can be a width proportional to this measurement time point, such that the proportionality factor can be situated, for example, in the range from 0.1 to 0.6 or more preferably in the range from 0.2 to 0.5. "Width" here can be considered, for example, as the half-value width of the relevant weighting function.

It is understood that in the inventive differential thermal analysis method, in addition to the sample temperature, one or more of the following values, for example, are particularly measured during tempering:

sample mass, a geometric dimension (e.g., length) of the sample, possibly with controlled mechanical impact an electrical property of the sample, for example a dielectric loss factor (or the reciprocal thereof, the "ion viscosity"), a magnetic property of the sample, a gas emission (amount and/or composition of content), for example while using a mass spectrometer and/or an FTIR spectrometer.

This type of measurements, including the measurement of the sample temperature as required in accordance with the invention, can be automated, such as in the framework of a program that controls the entire analytic method and that therefore, in particular, also can power a tempering device of the relevant analytic device to produce the essentially linear temperature program. By means of control software of this type, all calculation steps described here for determining the c-DTA signal can also be implemented.

The invention is described further hereinafter with reference to embodiments and the appended drawings, which are as follows.

DETAILED DESCRIPTION OF THE INVENTION

Figure 1:
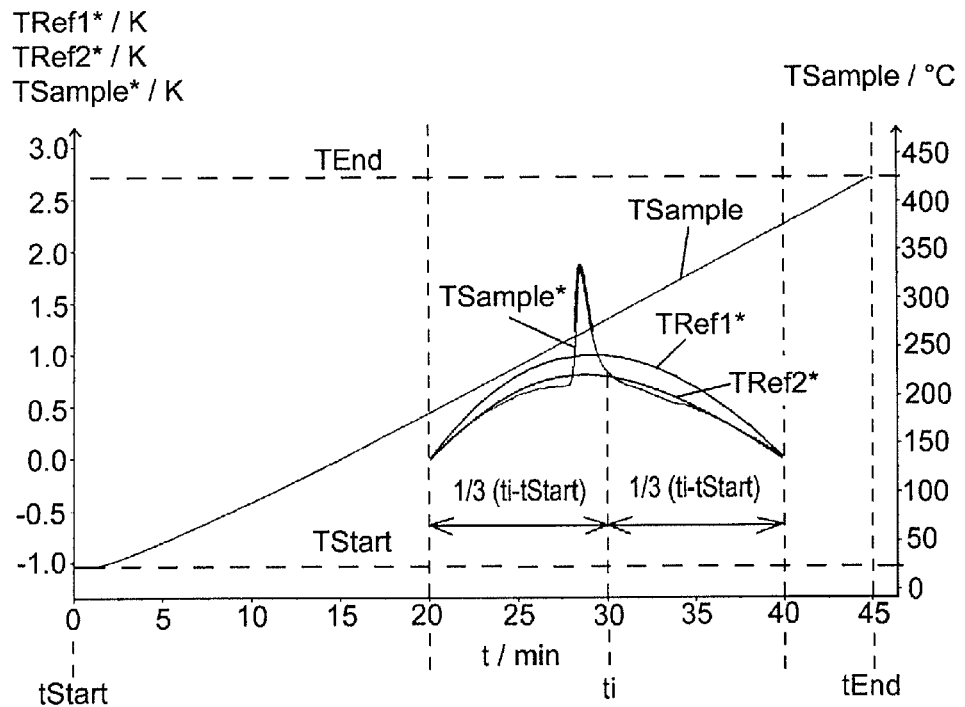
FIG. 1 shows a diagram to illustrate a temperature program conducted in a calculated differential thermal analysis (sample temperature $T_{Sample}$ depending on time t) and to determine a c-DTA signal c-DTA($t_i$) for a particular measurement time point ($t_i$).
Figure 2:
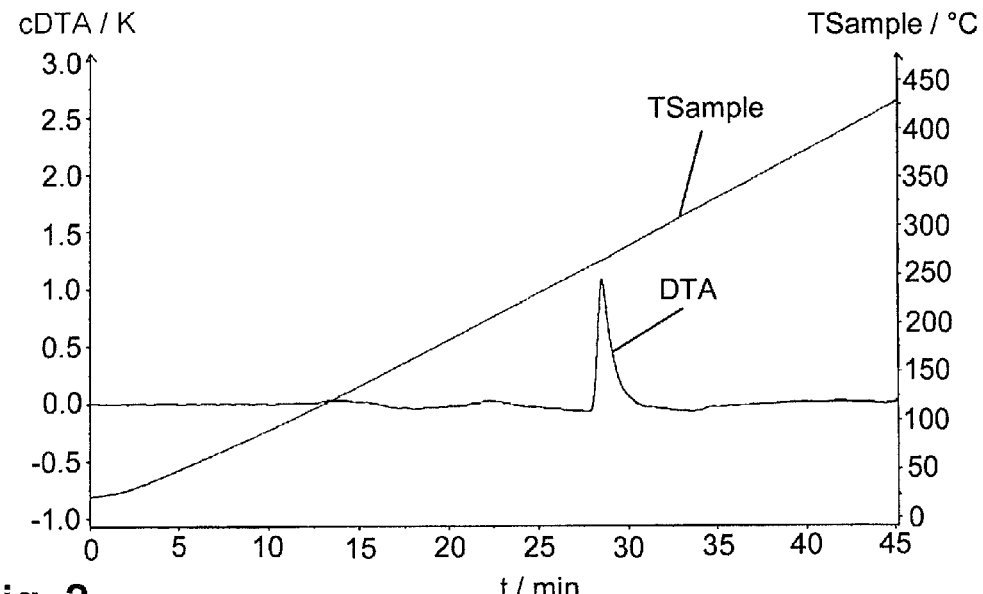
FIG. 2 shows a timing diagram corresponding to FIG. 1 that plots the c-DTA signal c-DTA(t) resulting for the entire duration of the temperature diagram.

FIGS. 1 and 2 illustrate a first embodiment of a method to perform a differential thermal analysis, in which a sample disposed in a temperable sample space (e.g., an electrically heatable and/or coolable furnace) is tempered according to an essentially linear temperature program, extending from a start temperature $T_{Start}$ to an end temperature $T_{End}$.

The tempering in the illustrated example is a heating of the sample (sample temperature $T_{Sample}$), from a start temperature of $T_{Sample}$=25° C. at a start time point $t_{Start}$=0 extending to an end temperature $T_{End}$=425° C. at an end time point $t_{End}$=45 min of the temperature program.

Such a linear temperature program, that is, to achieve an essentially linear temperature climb in the sample space in the period from $t_{Start}$ to $t_{End}$, can be performed in a manner known per se, by using an electrically heatable furnace (sample space), with programmed control and/or using a PID regulator or the like.

In very general terms, thermal analysis is a matter of investigating the behavior of samples or materials during modifications of temperature. A linear temperature modification of the sample space (e.g., interior of a furnace) causes a corresponding sample temperature $T_{Sample}$ with a time delay, and a corresponding linear modification of the sample temperature $T_{Sample}$ over time.

The sample temperature $T_{Sample}$ can be measured, for example, with a thermal element disposed on the sample or with other temperature measuring device suited to this purpose. This is a time-resolved measurement during tempering, at a number of measurement time points $t_0$ ($=t_{Start}$), $t_1$, $t_2$, $t_3$ ... $t_i$, ... $t_{n-2}$, $t_{n-1}$, $t_n$ ($=t_{End}$).

In addition, during tempering, in a manner known per se, other signals can be measured that are representative for certain parameters or features of the sample. Merely by way of example, such examples could include measurement of a change in mass (thermogravimetry), measurement of a length modification (dilatometry) or of length modification with controlled stressing (thermal-mechanical analysis), measurement of an ion viscosity change (dielectric analysis) as well as measurement of a gas emission (quantity and/or composition), for example while using a mass spectrometer or FTIR spectrometer.

Additional corresponding measurement values can be recorded and stored, for example, at the same measurement time points $t_0$, $t_1$, $t_2$, . . . as for temperature measurement.

For the determination and analysis of heat tones (enthalpy modifications) in the course of the sample tempering, for example conditioned by phase transmissions, it is already known a method from the aforementioned DE 199 34 448 A1, for instance. It is a known method to calculate a so-called c-DTA (calculated differential thermal analysis) signal from the result of the measurement during tempering of the sample temperature (compare $T_{Sample}$ in FIG. 1) as the difference between the measured sample temperature $T_{Sample}$ and a reference temperature $T_{Ref}$ calculated according to an idealized linearly recorded temperature curve. Those points in the time tempering process at which the c-DTA signal differs from zero can be interpreted as points with a heat tone (exothermal or endothermal depending on the sign of the difference).

If the known method were used to calculate the c-DTA signal in the example shown in FIG. 1, then the time-dependent C\c-DTA signal c-DTA(t) could be calculated as follows:

$$c\text{-DTA}(t) = T_{Ref}(t) - T_{Sample}(t)$$

where $$T_{Ref}(t) = T_{Start} + \beta \times (t - t_{Start})$$

such that $\beta = (T_{End} - T_{Start})/(t_{End} - t_{Start})$ applies; $\beta$ therefore is the median temperature modification rate over the tempering process, and such that $T_{Sample}(t)$ is the (actual) sample temperature measured by means of the thermal element.

It is disadvantageous here that a c-DTA signal not equal to zero, according to this known determination method, can arise also because of a non-linearity of the temperature program (unavoidable in practice), and therefore the DTA signal is more or less distorted by a non-linearity of this type.

According to the present invention, an improved method for calculating the c-DTA signal c-DTA(t) is used, which hereinafter is described in greater detail with reference to FIGS. 1 and 2 according to an embodiment.

In a first step, a time interval containing the relevant measurement time point is ascertained for every desired measurement time point (for which a value of the c-DTA signal is to be ascertained).

In FIG. 1, this determination of the time interval is illustrated by way of example for a determined time point $t_i$ ($t_i$=30 min). In the illustrated example, the position and width of the time interval is ascertained depending on the time difference between the first measurement time point $T_{Start}$ and the present, relevant measurement time point $t_i$, proportionally to this time difference.

In the illustrated example, the time interval starts a time span of ⅓×($t_i$−$t_{Start}$) before $t_i$ and ends a time span of ⅓×($t_i$−$t_{Start}$) after $t_i$. This time interval, which in the manner described hereinafter serves as an "evaluation range" for calculating the value c-DTA($t_i$), is plotted in dotted lines in FIG. 1. In the illustrated example it extends from t=20 min to t=40 min, such that the relevant measurement time point is thus situated in the middle of the time interval. The latter, however, is not at all necessary in the context of the invention. Instead, the relevant measurement time point can be situated at a certain distance from the time interval centerpoint, such that in this case the distance is preferably smaller than 30%, in particular smaller than 20%, of the time interval length.

In a second step, by using an appropriate adjustment or fit algorithm (such algorithms are known by now in the art), a non-linear adjustment function $T_{Ref1}(t)$ is calculated for the measured sample temperature curve $T_{Sample}(t)$ in the previously established time interval (here from 20 min to 40 min).

The algorithm being used can be configured, for example, in such a way that by means of the adjustment the sample temperatures $T_{Sample}$ at the start (t=20 min) and at the end (t=40 min) of the time interval are reproduced exactly; that is, in the illustrated example $T_{Ref1}(20\text{ min})=T_{Sample}(20\text{ min})$ and $T_{Ref1}(40\text{ min})=T_{Sample}(40\text{ min})$ applies. In general, however, it is preferable that the algorithm being used foresees no such exact adjustment of particular adjustment function values to certain actual sample temperature values, but rather provides an adjustment function adjusted as uniformly well as possible to all sample temperature measurement values, apart from the case, also described here, of an adjustment function with a weighting taken into account. In this respect, it is possible to use, for example, adjustment algorithms based on the "least square method."

The illustrated example employs as an adjustment function a second-degree polynomial, calculated for example by the least square method. Departing from this example, a higher-degree polynomial or other adjustment function could also be used.

FIG. 1 does not directly show the calculated adjustment function $T_{Ref1}$, but rather according to a modified illustrative manner an adjustment function $T_{Ref1}*$, which depicts the difference between a "straight line" through the two temperature measurement points bordering the time interval and the calculated adjustment function $T_{Ref1}$.

As can be seen from FIG. 1, for the curve of $T_{Ref1}*$ the result, corresponding to the adjustment function used here as a second-degree polynomial, is a parabola. The same is true for the shape of the adjustment curve $T_{Ref1}$ (not shown in FIG. 1), which is not based on the "straight line."

In a third step, in the aforementioned time interval those temperature measurement points are eliminated that are situated relatively "far off" from the ascertained adjustment curve (adjustment function $T_{Ref1}$). Likewise, plotted in FIG. 1 in the time interval is a temperature curve $T_{Sample}*$, which shows the sample temperature that is again based on the "straight line." The aforementioned elimination of temperature measurement points situated far off corresponds accordingly in FIG. 1 to an elimination of those points of the $T_{Sample}*$ curve whose temperature value diverges more strongly from the temperature according to the adjustment curve $T_{Ref1}*$.

In the illustrated example, all measurement points are eliminated, for example, in which the amount of the divergence $T_{Sample}-T_{Ref1}$ (synonymous with $T_{Sample}*-T_{Ref1}*$) is greater than 50% of the maximum divergence between these two curves in the time interval. In FIG. 1, a range of measurement points of the curve $T_{Sample}*$ that accordingly are to be eliminated is shown in boldface.

In a fourth step then, a corrected adjustment function $T_{Ref2}$ is calculated, as in the second step explained above, but disregarding the measurement points eliminated in the third step. In other words, again a non-linear adjustment function $T_{Ref2}$, here once again a second-degree polynomial, is calculated for the measured sample temperature curve $T_{Sample}$, but without the measurement points eliminated from this curve. As adjustment algorithm it is possible, for example, to use the same algorithm as was employed before in the aforementioned second step.

In FIG. 1, again, the result of this "corrected" adjustment, that is, $T_{Ref2}$, is not directly illustrated, but rather the corresponding curve $T_{Ref2}*$ based on the "straight line."

In the described example, certain temperature measurement points (situated "far away" from the ascertained adjustment curve) were eliminated in the third step, so that in the fourth step the subsequently calculated corrected adjustment function $T_{Ref2}$ occurs without these eliminated measurement points being taken into account. Alternatively to an elimination of particular temperature measurement points, in the third step as well a suppression of these measurement time points could be foreseen in such a way that, in the fourth step that was to be performed next, "less weight" was accorded to these measurement points situated far off than to other measurement time points. The adjustment function $T_{Ref2}$ calculated in the fourth step is thus adjusted in particular, or better, to the other (not far distant) measurement points, and less to the measurement points situated far off, corresponding to their lesser weight. In a refinement of this modification, it can be foreseen that the weight allotted in the third step for purposes of suppressing measurement points is allotted depending on a size that is representative for the particular divergence between the value of the temperature curve and the value of the adjustment curve (for the same time t).

In the present embodiment, the progression from $T_{Ref2}*$, equivalent with $T_{Ref2}$, is used in the following fifth step as the progression of a reference temperature for calculating c-DTA $(t_i)$. Contrary to this, however, the aforementioned third and fourth steps could be repeated once or even more often in order to calculate, accordingly, an adjustment function that is further corrected once or more often, such that the last calculated adjustment function is then used as reference temperature curve for the following fifth step.

In a fifth step, the reference temperature is calculated for the time point $t_i$ as a value of the adjustment function $T_{Ref}$ for the measurement time point $t_i$.

After performing the foregoing five steps, the resulting DTA signal value c-DTA$(t_i)$ for the measurement time point $t_i$ can be calculated as:

$$c\text{-DTA}(t_i)=T_{Ref2}(t_i)-T_{Sample}(t_i)$$

or equivalently $$c\text{-DTA}(t_i)=T_{Sample}*(t_i)-T_{Ref2}*(t_i)$$

The foregoing five steps and concluding calculation of the c-DTA signal value c-DTA$(t_i)$ are then performed for all desired additional measurement time points in order finally to receive the desired DTA signal c-DTA(t).

FIG. 2 shows the c-DTA signal c-DTA(t) that results for the illustrated embodiment for the entire duration of the temperature program, that is from $t_{Start}$ to $t_{End}$. The following should be noted here. In performing the aforementioned steps for measurement time points close to the end time point $t_{End}$, the time interval that is to be established in the first step extends beyond the end time point. However, to perform the fifth step, temperature measurement data are required in this area "beyond the time duration of the temperature program." These measurement points, which are "absent" in the measured data, are supplemented by an extrapolation, preferably a linear extrapolation, in the stored measurement data, so that the second step can be performed for all desired measurement time points.

Departing from the described embodiment, the aforementioned problems for measurement time points close to the end time point $t_{End}$ could also be resolved if the time interval is established in such a way (compare the "first step" described above) that its end (right-hand border) ends at $t_{End}$ at the latest. In other words, in this alternative embodiment, in the very first step the time interval is established so that it does not extend beyond $t_{End}$. The example described above for performing the first step, in which the time interval ends one time span of ⅓×($t_i$−$t_{Start}$) after $t_i$, can be modified in such a way for this purpose, for example, that the time span calculated in this way is necessarily so abbreviated (reduced) that it ends as early as at $t_{End}$.

In summary, the calculation of the c-DTA signal c-DTA(t) in the embodiment as in FIGS. 1 and 2 is based on the fact that for every desired measurement time point a separate adjustment curve (compare $T_{Ref1}$* or $T_{Ref2}$* in FIG. 1), for which in each case the measured temperature data are taken into account before and after the relevant measurement time point (compare the interval from ⅔×$t_i$ to ⁴⁄₃×$t_i$ in FIG. 1) and this calculation of the adjustment curve is repeated to some extent in the manner of a "sliding evaluation window" (with respect to the time axis) for all desired time points. The evaluation window width (duration of the established time interval), such as is the case in the embodiment described above, is preferably a function of the time position $t_i$. By combining the individual results (e.g., c-DTA($t_i$) from FIG. 1), one obtains the desired c-DTA signal c-DTA(t), as illustrated by way of example in FIG. 2.

Hereinafter, with reference to FIG. 3, a modified embodiment of a method for performing a calculated differential thermal analysis is explained, in such a way that the discussion is restricted to the differences from the embodiment described before.

The modification relates to the first two steps.

In these two steps, no time interval "with fixed borders" is established (first step) and then an adjustment function is performed for this time interval with equivalent consideration of all measurement points situated in the time interval (second step). Instead, in the modified embodiment in the second step the calculation of the adjustment function is performed, with consideration given to a weighting of the temperature data situated in the time interval. A maximum value of the weighting function used for this purpose is preferably given here, at least for the relevant measurement time point (or in its vicinity). In FIG. 3, by way of example, a Gaussian function F1(t−$t_i$) is plotted for the measurement time point $t_i$. This weighting function F1 reaches its maximum at the relevant measurement time point $t_i$ and is reduced with increasing distance from $t_i$.

The calculation, conducted in the second step, of the adjustment function for the time point $t_i$ accordingly takes into consideration the different weights of the individual measurement points within the established time interval. To this extent, it could be said in the modification that in the first step the time interval is established with "indistinct borders" rather than with "firm borders."

In a preferred configuration, for every measurement time point a width, for example a half-power width, is foreseen in the illustrated Gaussian function F1, and this width is established depending on the relevant measurement time point. In one embodiment, for example, it is foreseen that, the later the relevant measurement time point is situated, the greater the width of the weighting function is selected. The width can, for example, be selected proportionately to the relevant measurement time point (based on the start time point of the temperature program).

Departing from the described embodiment in which a symmetrical weighting function (here: a Gaussian function) was selected, this weighting function can also be asymmetrical in the framework of the invention.

Figure 3:
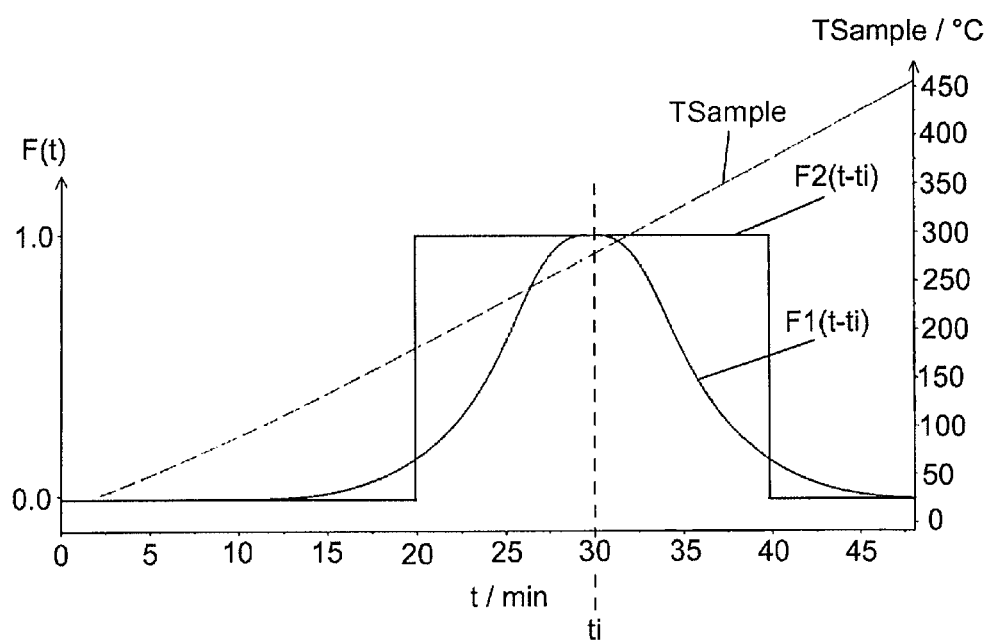
FIG. 3 shows a timing diagram that, along with the measured sample temperature $T_{Sample}$, also plots a weighting function F(t), used according to a modified c-DTA determination, for the modified calculation of a c-DTA value c-DTA ($t_i$) for a particular time point ($t_i$).

If, instead of the Gaussian function F1, a right-angle function F2, likewise plotted in FIG. 3, is used as the weighting function, then the method would again correspond to the method according to the embodiment described above. Weighting with a right-angle function, in the final analysis, is equivalent to establishing a time interval "with firm boundaries" (corresponding to the flanks of the right angle). Of particular interest, therefore, from the viewpoint of the modified embodiment, are weighting functions with a shape departing from the right-angle form, especially with monotonically or strictly monotonically decreasing weight of the weighting function as the distance from the relevant measurement time point increases. To that extent, the Gaussian function F1 explicitly illustrated in FIG. 3 is to be understood merely by way of example. Instead, for instance, a triangular function, trapezoidal function or the like could be used.

The remaining steps in the method of the modified embodiment correspond to the steps described above with reference to FIGS. 1 and 2.

With this modified method as well, a qualitatively very valuable c-DTA curve (time-dependent c-DTA signal) can be calculated for a desired time period, in particular for the entire duration of the sample tempering.

What is claimed is:

1. A method for performing a differential thermal analysis, in which a sample disposed in a temperable sample space is tempered according to a temperature program extending from a start temperature to an end temperature, such that, from a result of a measurement of a sample temperature conducted during the tempering at a number of measurement time points, a c-DTA signal is calculated as the difference between measured sample temperature and a reference temperature calculated according to a temperature curve model, wherein for every measurement time point the relevant reference temperature is calculated by means of the following steps:
a) establish a time interval containing the relevant measurement time point,
b) calculate a non-linear adjustment function for the measured sample temperature curve in the time interval, and
c) calculate the reference temperature as a value of the adjustment function for the measurement time point.

2. The method according to claim 1, wherein in step a), a beginning of the time interval is established by one time span, which depends on the measurement time point, before the relevant measurement time point.

3. The method according to claim 1, wherein in step a), an end of the time interval is established at one time span after the relevant measurement time point, which depends on the measurement time point.

4. The method according to claim 1, wherein in step a), a length of the time interval is established depending on the measurement time point.

5. The method according to claim 1, wherein in step a), in the event of the time interval extending before a start time point or after an end time point of the temperature program for conducting step b), an extrapolation is conducted on the sample temperatures that are to be used before the start time point or after the end time point.

6. The method according to claim 5, wherein the extrapolation is a linear extrapolation.

7. The method according to claim 1, wherein in step b), a second-degree polynomial is used as the adjustment function.

8. The method according to claim 1, wherein step b) further comprises by the following steps:
suppress measurement time points for which the measured sample temperature diverges by more than a predetermined amount from the relevant value of the adjustment function, and calculate a corrected adjustment function to use in step c), as in step b), but disregarding or underweighting the suppressed measurement points.

9. The method according to claim 1, wherein in step b), the calculation of the adjustment function is performed taking into account a weighting of the sample temperatures situated in the time interval.

10. The method according to claim 1, wherein the temperature program is an essentially linear temperature program.

* * * * *